US006284814B1

(12) United States Patent
Gupta

(10) Patent No.: US 6,284,814 B1
(45) Date of Patent: *Sep. 4, 2001

(54) METHOD OF MAKING MASTERBATCHES OF LIQUID ADDITIVES AND, IN PARTICULAR, ANTIMICROBIAL MASTERBATCHES

(76) Inventor: Chakra V. Gupta, 208 5th St., NE., Conover, NC (US) 28613-2041

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/143,741

(22) Filed: Aug. 31, 1998

(51) Int. Cl.$^7$ .................................................. C08K 5/521
(52) U.S. Cl. ................................................... 523/122
(58) Field of Search ...................... 523/351, 122

(56) References Cited

U.S. PATENT DOCUMENTS

| | | |
|---|---|---|
| 3,531,433 | 9/1970 | Elmer . |
| 3,942,773 | 3/1976 | Csonger . |
| 3,976,608 * | 8/1976 | Buckler ................................... 260/4 |
| 3,985,661 * | 10/1976 | Ikeda ..................................... 252/12 |
| 3,987,007 | 10/1976 | Kalogris . |
| 4,556,603 * | 12/1985 | Thorsrud ............................... 428/283 |
| 4,652,138 | 3/1987 | Inoue et al. . |
| 4,674,885 * | 6/1987 | Erwin ..................................... 366/76 |
| 4,710,535 * | 12/1987 | Perrot ..................................... 524/413 |
| 4,725,657 | 2/1988 | Shibanai . |
| 4,900,156 | 2/1990 | Bauer . |
| 4,921,670 * | 5/1990 | Dallmann ............................. 264/141 |
| 4,938,955 | 7/1990 | Niira et al. . |
| 4,940,735 * | 7/1990 | Kress ..................................... 521/86 |
| 5,208,016 | 5/1993 | Ohmae et al. . |
| 5,318,358 | 6/1994 | Wobbe et al. . |
| 5,348,388 | 9/1994 | Geyer . |
| 5,358,979 | 10/1994 | Van Hoboken et al. . |
| 5,482,989 | 1/1996 | Koskiniemi . |
| 5,487,602 | 1/1996 | Valsamis et al. . |
| 5,516,814 | 5/1996 | Trotoir . |
| 5,614,568 | 3/1997 | Mawatari et al. . |

* cited by examiner

Primary Examiner—Paul R. Michl
(74) Attorney, Agent, or Firm—Alston & Bird LLP

(57) ABSTRACT

A method for introducing relatively large quantities of liquid additives into polymer-containing composition includes increasing the free volume between polymer chains of the polymer(s) present in the composition and introducing at least one liquid additive into the free volume between the polymer chains. The method can optionally include the introduction of low melting additives into the polymer This method allows for the production of polymer masterbatchs from a wide variety of liquid additives that can contain upwards of 50% by weight active components. Such masterbatches can be a particularly useful technique for introducing biocides and/or antimicrobials into polymeric materials.

14 Claims, 1 Drawing Sheet

METHOD OF MAKING MASTERBATCHES OF LIQUID ADDITIVES AND, IN PARTICULAR, ANTIMICROBIAL MASTERBATCHES

FIELD OF THE INVENTION

A method for introducing relatively large quantities of liquid additives into polymer-containing compositions can be used to provide a masterbatch composition suitable for use in a variety of polymer-containing compositions. For example, the masterbatch compositions can be used in molded resin articles, nonwoven fabrics and paints. The masterbatches find particular usefulness as a method for introducing biocides and antimicrobials into these compositions.

BACKGROUND OF THE INVENTION

Over the years, polymers have been widely used in both household and industrial applications. For example, the surface appearance, physical and mechanical properties of polystyrene resins have made them popular in a variety of fields including electronics, automobiles, as well as sundry and sanitary items. Similarly, polyolefins such as polyethylene and polypropylene, have been widely used in extrusion and injection molding applications.

The art has long sought to introduce additives, both liquid and solid, into polymers. To this end, masterbatches, e.g., solid dyes and pigments in a polymer matrix, have been used to introduce solid additives, e.g., a desired color, into a polymer.

Alternatively, liquid active ingredients have been introduced into the polymer compositions in order to provide or enhance a desired property of polymer compositions. Examples of "active" liquid agents include bactericides, perfumes, insectifuges, rust preventatives, mildew-proofing agents, and antimicrobials, among others.

One particularly significant problem faced in producing extruded or molded articles from resin materials has involved bacterial and microbiological fouling. This problem can be particularly pronounced since resins are often used in high moisture and humidity environments that serve as excellent breeding grounds for unwanted microorganisms such as bacteria, mold, fungi and mildew.

In an attempt to address this problem, a variety of processes have been developed each of which seek to introduce an antimicrobial or biocide agent into a molded resin article. In this regard, it has been proposed to mix the desired agent into the synthetic resins material prior to formation of the molded articles. Alternatively, processes have involved introducing the agent during or subsequent to formation of the articles. Examples of such process include applying the desired active agents onto the surface of the synthetic resin product, injecting the agent into a "space" within a formed resin product or laminating the agent between layers or sheets of the resin(s).

Specific techniques for introducing antimicrobial agents and/or biocides into polymer resins have been disclosed in U.S. Pat. No. 3,531,433, to Elmer, U.S. Pat. No. 3,987,007, to Kalogris, U.S. Pat. No. 4,725,657 to Shibanai, U.S. Pat. No. 4,938,955 to Niira et al., U.S. Pat. No. 5,205,016 to Ohmae et al., U.S. Pat. No. 5,358,979 to van Hoboken et al., U.S. Pat. No. 5,482,989 to Koskiniemi, U.S. Pat. No. 5,516,814 to Trotoir, and U.S. Pat. No. 5,614,568 to Mawatari et al.

These techniques, however, have suffered from a variety of disadvantages. For example, attempts to introduce the active agents into the resins themselves have been faced with problems such as poor heat stability, toxicity, and a short life. Thus, these techniques have not proven entirely effective in providing a polymer product having the desired antimicrobial effect.

Moreover, these techniques are often severely limited in terms of the types and amounts of antimicrobial agents that may be introduced into the resin. For example, conventional processes using extruders to mix a polymer with an additive are significantly limited in terms of the polymers and additives that can be used. That is, where melting point for a resin is greater than the boiling point for a liquid additive, the components are said to be incompatible because the temperatures needed in the extruder would prevent the additive from becoming mixed with the resin.

One solution to this problem has involved the modification of the extruder so as to introduce certain additives immediately preceding the point where the polymer exits the extruder. While this arrangement has only worked for certain lower boiling point additives, it is also extremely limited in terms of the amounts of additive that may be introduced into the polymer. Moreover, it requires the use of very specialized equipment that increases production costs.

Even in those situations where the polymer and additive may be "compatible", the amount of additive is typically limited to 5 weight percent or less, although as much as 10 weight percent has been suggested under certain limited conditions.

Recent attempts to increase the amount of the liquid additive have focused on the use of carriers, e.g., plasticizers such as those disclosed in U.S. Pat. No. 5,358,979, for the active agent, in this case, microbiocides. However, such carriers have introduced their own set of problems regarding the use and handling of the resulting masterbatch.

Accordingly, the need still exists for a method which is capable of providing increased amounts of liquid active component in a polymer without the need for carrier materials.

SUMMARY OF THE INVENTION

Among other factors the present invention is based on the surprising discovery that the suitable relaxation of a polymer can allow for the introduction of relatively large amounts of liquid additives without the need to employ a carrier material. This method makes possible the manufacture of a masterbatch that is easy to store, use and transport, and that can be used in a variety of polymer-containing compositions.

In one preferred aspect, the present invention relates to a method for making a masterbatch composition containing a polymer and one or more active agents present in an amount not less than 10% by weight of the composition. Moreover, the masterbatch is preferably at least substantially free of any carrier component for the active agent. This method preferably comprises the steps of:

(1) increasing the free volume between the chains of one or more polymers by, e.g., relaxing the desired polymer (s);

(2) introducing one or more liquid additives into the polymer(s) under conditions effective to provide a homogeneous mixture of the polymer(s) and the additive(s); and (3) providing a sufficient residence time for the mixture, with optional gentle mixing, to allow the additive to enter the voids in the polymer(s).

Typically, step (1) involves melting of the polymer(s) while step (2) involves mixing of the polymer(s) and additive(s). In addition, Steps (2) and (3) can be repeated at least once, and preferable two or more times, depending on the nature of the polymer and the additive as well as the quantity of additive which is desired.

A preferred device for practicing this method is a twin screw extruder, and in particular, an extruder which employs a sequence of kneading (dispersive mixing) elements as well as turbine (or distributive mixing) elements in connection with step (2).

This method can be employed with a wide variety of polymers, active agents that, at ambient temperatures, are in either liquid or solid form. One example of a masterbatch produced by the inventive process comprises, as the polymer, a polyolefin, e.g., polyethylene, polypropylene, or copolymers thereof a polystyrene or a polyester and, as the active agent, an antimicrobial agent that is at least substantially free of heavy metals, arsenic, halogens, phenyls and formaldehydes, such as INTERSEPT® microbial agent.

Moreover, one or more non-carrier additives can be introduced into the polymer, prior to (2), in order to modify the melting point of the polymer mixture. This will increase the capability of the polymer(s) and allow for a more widely varied group of additives.

Other aspects of this invention include masterbatch compositions themselves as well as polymer-containing compositions produced from these masterbatch compositions.

DETAILED DESCRIPTION OF THE PREFERRED EMBODIMENT

Figure 1A:
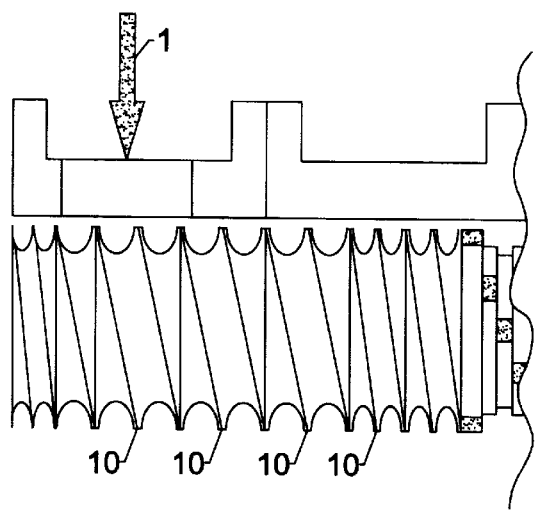
FIGS. 1a–c illustrate a schematic view of an extruder suitable for practicing the inventive method.

As discussed above, the invention includes a method capable of introducing large quantities of liquid additive(s) into one or more polymers. This method can provide masterbatch compositions that include relative large amounts, e.g., upwards of 20% by weight, of these liquid agent(s).

The inventive method includes two aspects, (i) increasing the free volume between polymer chains in a composition and (Ii) introduction of the desired liquid additive into the free volume.

The first of these steps, increasing the free volume, typically involves relaxation of the desired polymer. The typical techniques for polymer relaxation involves shearing or melting of the polymer. This shearing or melting is performed under conditions sufficient to provide for an increase in free volume between the polymer chains. The specific conditions are dependent on the particular polymer employed.

The melting and/or shearing can be performed by techniques well recognized in the art such as extruders including single screw, twin screw, co-rotating and counter-rotating twin screw extruders. These extruders employ art-recognized conveying elements to move the polymer though the extruder while heating the polymer. Suitable elements for use in the extruder are commercially available from suppliers such as Werner & Pfleiderer Co., Berstorff Co., Leistritz Co. and Theysohn Co. and as such are well recognized in the art.

The polymer that can be employed in this invention is limited in choice only by the requirements of the resulting product. Suitable polymers can have a melt index ranging from the fractional, i.e., less than 1, to the very high, e.g, upwards of 300 or greater with melt indexes of 15–50 being preferred in many instances.

For sake of completeness, it should be noted that a wide variety of polymers are commercially available. In order to illustrate this point, an extensive list of tradenames for commercially available polymers can be found on the Internet at www.geocities.com\~spanoudi\tradename.html. This list is incorporated by reference in its entirety.

Although not limited thereto, for many of the preferred applications the polymer component is typically selected from among polyolefins, e.g., polyethylenes, polypropylene, and copolymers thereof, polystyrenes and polyesters.

The particular polymer(s) employed is dependent only upon the resulting end product. For example, where the process served to provide a masterbatch to be used in extrusion and injection molding applications, polyolefins, e.g., polyethylene such as LDPE, LLDPE and HDPE, and polypropylene are often preferred. In a specific example, where a nonwoven fiber is to be produced, high flow polypropylene can be preferred. In this regard, isotactic or syndiotactic polypropylene homopolymers, copolymers, or terpolymers can all be used. Examples of commercially available polypropylene polymers include polymers available under the SOLTEX tradename, MONTELL tradename, Exxon tradename, AMOCO Tradename and ARISTECH tradename. On the other hand, where a masterbatch is to be used in paint compositions, polystyrenes are often preferred. Of course, more than one polymer can be employed in the inventive composition.

The inventive method can further be used in those instances where the polymer is "not" compatible with the desired additives. By "not" compatible it is meant that the polymer has a melting point or glass transition temperature that is greater than the boiling point of the liquid additive so that the additive will, in effect, evaporate if introduced into the melted polymer.

In such situations, the polymer(s) can be modified to provide a suitable compatibility. Examples of suitable modifying components include waxy materials such as polypropylene esters available under the Arylzene tradename from Georgia Pacific as well as diols and polyols such as polyester diols or polycaprolactone diols available under the Rucoflex tradename (e.g., Rucoflex S-102-55) from Ruco Polymers.

In this regard, a modifying component can be added in an amount effective to alter the melting point or glass transition temperature to a level suitable for use with the desired additive. Typically such an amount is not greater than 50% by weight of the polymer/modifying component mixture, preferably not greater than about 30% by weight of the mixture.

The second aspect of this method involves the introduction of a liquid additive into free volume between polymer chains. This aspect typically involves a two step process of mixing of the desired additive so as to provide a substantially homogeneous composition followed by soaking, with optional gentle mixing, of the homogeneous mixture for a time sufficient to allow the additive to enter the free volume in the polymer composition.

Although the additives can be virtually any desired component that can be introduced in liquid form into the polymer, the use of one or more "active" ingredients is preferred. By "liquid" form, it is referring to the state of the additive at that point in time when it is introduced into the polymer(s). For example, the additive can be in liquid form at room temperature or can be melted prior to introduction into the polymer.

By "active" ingredients or agents it is meant an agent which is capable of altering one or more property of the polymer and/or providing one or more property to the polymer. Examples of "active" ingredient in the context of the present invention include antimicrobial agents and bactericides as well as insectifuges, rust preventatives, mildew-proofing agents, dust mite killers, lubricants and fragrances. However, any additive that meets the functional requirement discussed above may also be used in the invention.

The preferred agent is an antimicrobial or antibacterial agent. The antimicrobial or antibacterial agents that can be employed in this masterbatch composition according to the invention include any of the numerous agents recognized in the art that can be introduced into the polymer in a liquid form or in a liquid carrier. For example, organo-copper compounds, organo-tin compounds, and chlorinated phenols have been used. Specific examples of compounds include copper naphthenate, copper-8-hydroxyguinolinate and pentachlorophenol esters such as pentachlorophenyl laurate.

Antimicrobial agents are also disclosed in U.S. Pat. Nos. 5,614,568; 2,919,200; 3,345,341; 3,959,556; 3,279,986; 4,891,391; and 4,624,679, which are incorporated herein in their entirety for all purposes.

However, for many household and industrial applications, it is preferred that the antimicrobial agents are:

(i) at least substantially free of heavy metals and arsenic; and/or (ii) at least substantially free of halogens, phenyls and formaldehydes.

One particularly preferred example of an antimicrobial agent which meets both of the foregoing properties is marketed under the name INTERSEPT® microbial agent by Interface Specialty Products, Kennesaw, Ga. INTERSEPT® is a proprietary synergistic blend of substituted ammonium salts of alkylated phosphoric acid and free alkylated phosphoric acid.

Liquid additives other than biocides may be used. In this regard, the following list is not meant to be exhaustive but merely illustrative of suitable additives that are recognized in the art. The choice of a particular additive is clearly dependent on the particular polymer and ultimate end use for the masterbatch.

Mildew proofing agents include those agents having an antibacterial and bactericidal effect. Examples of a substance which mainly serves as an antibacterial agent or a bactericide are chlorhexydine gluconate $(C_{22}H_{30}Cl_2N_{10}2C_6H_{12}O_7)$, N—(fluorodichloromethylthio) phthalimide and a-bromocinnamaldehyde $(C_9H_2OBr)$. Examples of compounds available primarily for a mildew-proofing function include thiabendazole; 2-hydroxydiphenyl; N-dimethyl-N'-phenyl-(N'-fluorodichloromethylthio)sulfamide; 3-methyl-4-chlorophenol; tolyltriazole; and benzotriazole.

Common insectifuges include not only repellents such as citronella oil but also those having an insectifugal and insecticidal effect. An example of an organic phosphorus insecticide suitable for use in the invention is fenitrothion (O, O-dimethyl) O-(3-methyl-5-nitrophenyl) thiophosphorate. Examples of the pyrethroid insecticides include allethrin; phthalthrin; resmethrin (benzyl-3-furyl)methyl dl-cis/trans-chrysanthemate; furamethrin; Phenothrin; permethrin; and 2-(4-ethoxyphenyl)-2-methylpropyl 3 phenoxybenzyl ether.

Examples of common rust preventives include volatile rust preventives or volatile rust preventive oils such as dicyclohexylammonium nitrite, di-isopropylamine nitrite and ferro-bright oil.

Examples of common fragrances include both natural and synthetic perfumes. Examples of natural perfumes are animal or vegetable perfumes such as lavender oil, citronella oil, rose oil, lemon oil and jasmin oil. Examples of synthetic perfumes are ethyl acetoacetate $(C_6H_{10}O_3)$, acetophenone $(C_8H_8O)$, anisic aldehyde $(C_8H_8O_2)$, benzyl benzoate $(C_{14}H_{12}O_2)$, amyl cinnamic aldehyde $(C_{14}H_{18}O)$, methyl benzoate $(C_8H_8O_2)$, ethyl isovalerate $(C_7H_{14}O_2)$, ethyl vanillin $(C_9H_{10}O_3)$, ethylene brassylate $(C_{15}H_{26}O_4)$, ethyl formate $(C_3H_6O_2)$, citronellyl formate $(C_{11}H_{20}O_8)$, coumarin $(C_9H_6O_2)$, cuminaldehyde $(C_{10}H_{12}O)$, cinnamyl alcohol $(C_9H_{10}O)$, geraniol $(C_{10}H_{18}O)$, acetyl eugenol $(C_{12}H_{14}O_3)$, citronellyl acetate $(C_{12}H_{22}O_2)$, terpnyl acetate $(C_{12}H_{20}O_2)$, benzyl acetate $(C_9H_{10}O_2)$, isoamyl salicylate $(C_{12}H_{16}O_3)$, benzyl salicylate $(C_{14}H_{13}O_3)$, cyclamen aldehyde $(C_{13}H_{18}O)$, citral $(C_{10}H_{16}O)$, citronellol $(C_{10}H_{20}O)$, tetrahydrolinalool $(C_{10}H_{22}O)$, terpineol $(C_{10}H_{18}O)$, vanillin $(C_8H_8O_3)$, ethyl phenylacetate $(C_{10H12}O_2)$, heliotropin $(C_6H_6O_3)$, musk ambrette $(C_{12}H_{16}O_5N_2)$, p-methylacetophenone $(C_9H_{10}O)$, methylionone $(C_{14}H_{22}O)$, ethyl methyl phenylglycidate $(C_{12}H_{14}O_3)$, 1-menthol $(C_{10}H_{20}O)$, butyric acid $(C_4H_8O_2)$, linalool $(C_{10}H_{18}O)$, linonene & dipentene $(C_{10}H_{16})$, rosephenone $(C_{10}H_9Cl_3O_2)$ and rosinol $(C_{10}H_{20}O)$.

The lower limit of active component introduced into the polymer is dependent on the amount needed to provide the desired property in the final product. However, one important advantage of the present invention involves the ability to introduce relatively large amounts of liquid additives into the polymer-containing masterbatch. Accordingly, it is preferred that the active(s) agent be present in an amount not less than 10% by weight of the composition, preferably at least 20% by weight.

As an upper limit, the amount of active component introduced into the polymer is dependent upon the property or properties provided by the particular active component in both the masterbatch and the desired end product. Typically, however, it is preferred that the agent(s) be present in an amount not greater than about 50% by weight. Although amounts greater than 50% can be employed, the resulting products can have undesirable physical characteristics, e.g., the composition can be slippery to the touch.

In contrast to prior art techniques, the method is capable of introducing the additives into the polymer without the use of carrier components. In fact, masterbatch compositions produced by this method are preferably at least substantially, if not completely, devoid of any carrier components for the active ingredient.

By "carrier components" it is meant any liquid and/or solid substances that provide, either physically or chemically, for the dissolution of the active components in the polymer compositions. Examples of those carriers that aid physically, include, but are not limited to, liquid solutions such as those discussed in U.S. Pat. No. 3,987,007, and solid materials such as those discussed in U.S. Pat. No. 4,663,359. Carrier components that aid "chemically" include materials that react with the active agent to aid in its dissolution. Examples of such materials include the polymers disclosed in U.S. Pat. No. 5,208,016, and the zeolites discussed in U.S. Pat. No. 4,938,955.

By "at least substantially devoid" it is meant an amount less than that needed for the component to act as a carrier for the active agent in the context of the masterbatch composition. That amount is typically less than 0.05% by weight.

For many applications, and for cost considerations, it is preferred that the polymer compositions be "neat", i.e., include only the polymer(s) and active agent(s). However, additives such as antioxidants, UV stabilizers, flame retardants and heat stabilizers can also be present, with the particular additives depending on the ultimate product.

Although discussed as separate steps, the additive introduction and soaking/gentle mixing steps can be performed in a single mixing device. Examples of standard mixing devices suitable for use in this invention include high speed and static mixers, such as:

1) Extruders including single screw, twin screw and counter rotating twin screw extruders,
2) Banbury® mixers, and
3) Farrel® continuous mixers.

Extruders, and particularly, twin screw extruders are preferred. In fact, the use of extruders allows the second aspect of the invention to be performed in the same device as the first aspect of the process. That is, a single extruder can be used to perform each of the steps of the inventive method.

Although design of our extruder would be dependent on the particular polymer/additive combination, a typical extruder would preferably include 4–15 barrels, with 6–10 barrels being more preferred. As was the case with the first aspect, suitable mixing and conveying elements for use in the extruder are commercially available to those skilled in the art. For example, the introduction of a low melting additive preferably involves the use of distributive mixing elements, e.g., turbine elements, and/or dispersive mixing elements, e.g. kneading elements. Such elements are commercially available from a number of suppliers including Werner & Pfleiderer Co., Berstorff Co., Leistritz Co. and Theysohn Co. The number and arrangement of these elements used in this aspect of the process depend on the particular components employed in the process, however, they are selected to provide for a homogeneous mixture of the polymer(s) and additive(s).

As to the soaking/gentle mixing step, the extruder can employ those commercially available conveying and/or mixing elements recognized in the art. The number and arrangement of these elements are selected to provide a sufficient time and environment for the additive to "soak" into voids present in the "relaxed" polymer. The particular length of time needed to allow the sufficient soaking of the active component into the polymer is dependent on the type and amount of active agent and the particular polymer(s) being employed. For example, in a preferred embodiment discussed below which involves the use of polyolefins and an antimicrobial agent, a typical residence time is from 1–10 minutes, preferably 2–5 minutes.

The extruder would include one or more inlet(s) for the polymer and one or more inlets for the low viscosity additive(s) at ambient temperatures. Moreover, typical operating conditions would involve screw speeds of 100–600 rpm, preferably 400–600 rpm.

The additive introduction and soaking steps can be repeated one or more times, as desired, in order to modify the amount of additive being introduced into the polymer or introduce more than one additive into the polymer.

As discussed above, a primary use for the inventive method is in making masterbatch compositions. A masterbatch composition typically involves the formation of pellet size particles containing the desired additive which pellets are then introduced into a polymer during subsequent processing. The pellets allow for the easier handling of the desired active components.

In the inventive method the mixture can be finely divided subsequent to soaking to provide a masterbatch composition. One example of a method of finely dividing the polymer includes pelletization and micropelletization. Both pelletization and micropeletization can occur by techniques recognized in the art, e.g., a suitable dies on extruder, and as such need not be described in detail here. In this regard, a typical particle size for pelletization ranges from 0.05"×0.05" to 0.15"×0.15" with micropelletization providing particles on the order of 0.01"×0.01".

Alternatively, the masterbatch can be further pulverized to form a fine powder and used in various solutions and suspensions, such as paints. In this regard, the powder size is typically on the order of 15–200$\mu$. In this embodiment, the powder can be as an additional additive to the composition or a replacement for existing active components in the compositions. An example of a suitable paint composition is illustrated in Example 15 of this specification.

The masterbatch composition of the present invention can be used in the same manner as traditional dye and pigment masterbatch compositions. In this regard, the masterbatch compositions can be used in connection with polymer-containing compositions that are either in liquid or solid form. In each case, the masterbatch is employed in an amount effective to provide the desired property to the polymer-containing composition with the amount of the masterbatch employed is dependent on the amount of active material in the masterbatch, the nature of the active material and the final product. Specific examples of suitable uses for the masterbatch compositions include the fields of extrusion and injection molded materials.

The masterbatch can be used directly or can be subject to treatment prior to its use. For example, in making woven or nonwoven fibers, where an antimicrobial agent is employed as the active ingredient, it is preferred that the masterbatch be added to a polymer in an amount effective to provide a final product having about 1–10% by weight, preferably 1–5% by weight, of the antimicrobial agent. To this end, where the active agent is present in amount of about 20% by weight of the masterbatch, about 7–15% by weight of the masterbatch is preferably used to provide the final product. In yet another example, a paint composition may include 1–10% by weight of the masterbatch.

The masterbatch compositions according to the present invention are capable of providing a number of advantages over existing compositions. First of all, the present invention is capable of introducing relatively large amounts of liquid agents into a polymer resin without the need to employ any carrier materials. This not only decreases the cost of the product but makes it easier to produce. Moreover, the increased loading of liquids in the masterbatch means that less masterbatch has to be employed in providing the desired properties to the final product. Finally, the use of masterbatches in connection with liquid additives is an improvement in terms of both handling and use on the liquid compositions themselves.

For sake of clarity, this specification will now focus on one specific example of a masterbatch according to the invention that involves the use of antimicrobial agents. The invention in this regard is capable of introducing relatively large amounts, i.e., greater than 10% by weight, of liquid antimicrobial agents into a polymer, e.g., polyolefin material. While the following discussion may focus on this combination of antimicrobial agents with polyethylene, polypropylene, and copolymers thereof, those skilled in the art would recognize that this discussion is equally applicable to other combinations of polymer(s) and active agent(s).

This embodiment of the invention preferably comprises polyolefins, and the antimicrobial agent INTERSEPT®. Moreover, the antimicrobial is present in an amount of 10–50% by weight of the composition, preferably 20–40%.

Figure 1B:
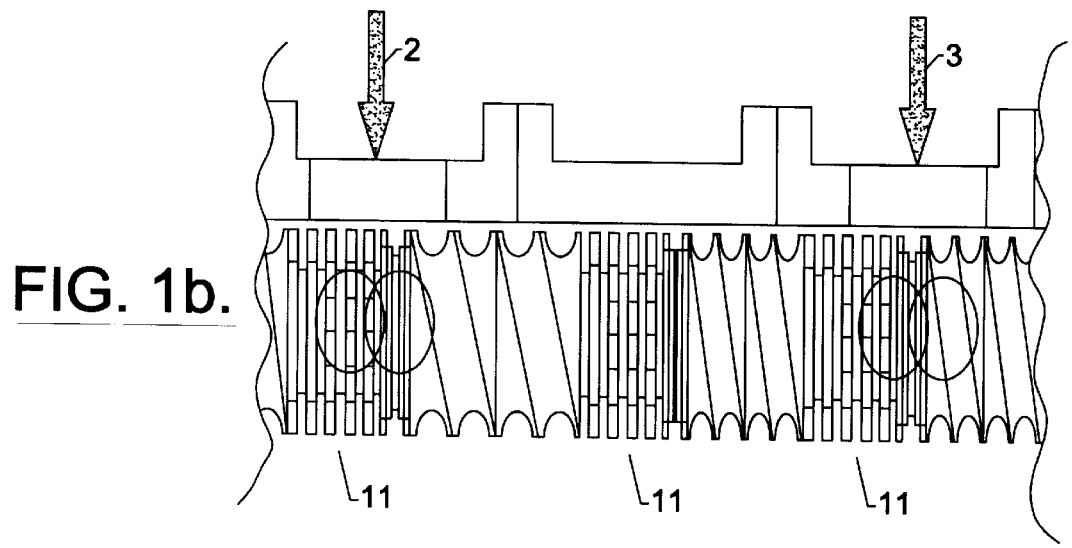
Figure 1C:
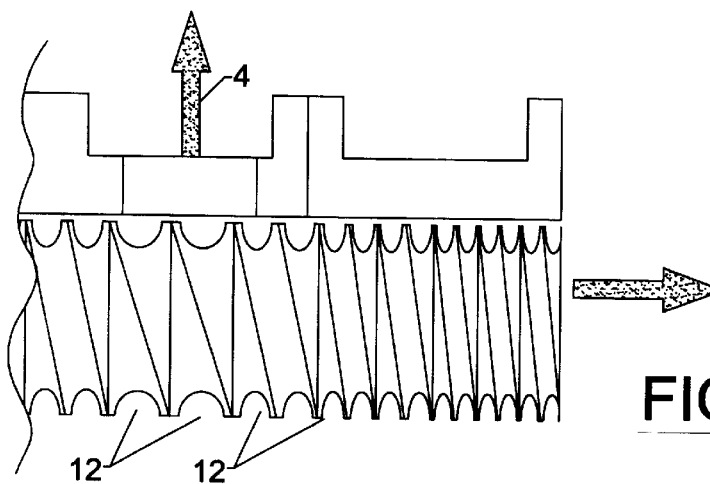

One specific example of a technique for providing the inventive involves the use of a twin screw extruder that includes melting section followed by a plurality of mixing zones and soaking zones, as illustrated by FIGS. 1a–1c. This extruder arrangement will be discussed in three parts, melting of the polymer (FIG. 1a), intimate mixing of additive and the polymer (FIG. 1b), and providing a suitable residence time for allowing the active ingredient to soak into the polymer (FIG. 1c).

As illustrated by FIG. 1a, the polymer 1 is melted in the extruder. The polymer is then conveyed through the section by way of elements 10. Specific examples of such conveying elements include Werner & Pfleiderer 60/60 and 90/90 conveying elements.

The melted polymer is then mixed with the additives in the section illustrated by FIG. 1b. In this section, the melted polymer is then mixed with additives 2 and 3 by way of distributive mixing elements 11 to provide a homogeneous mixture. Specific examples of such elements are Werner & Pfleiderer TME 0/20 and 45/20 turbine mixing elements.

The mixture then enters the soaking/gentle mixing section illustrated by FIG. 1c. In this section, the additive is allowed to fully soak into the voids in the relaxed polymer while being conveyed to the extruder outlet by way of elements 12. Once again, elements such as Werner & Pfleiderer 45/45, 60/60, and 90/90 can be employed to convey the polymer mixture The section can also provide for communication with a vacuum source provided by way of vent 4.

This embodiment of the invention will now be illustrated in terms of certain specific examples. However, it should be recognized that these examples are offered solely to illustrate this aspect of the invention but, in no way, to limit the invention

EXAMPLES 1–12

The following Examples 1–12 illustrate the formation of masterbatches in accordance with the invention. Masterbatches were produced in a 9 barrel, twin-screw extruder of FIGS. 1a–c containing 52 of the following elements:

| Element Type | Manufacturer | Label/Part No. |
|---|---|---|
| Conveying | Werner & Pfleiderer | 45/45 |
| Conveying | Werner & Pfleiderer | 90/45 SK-N |
| Conveying | Werner & Pfleiderer | 90/90 |
| Conveying | Werner & Pfleiderer | 60/30 LH |
| Conveying | Werner & Pfleiderer | 60/60 |
| Conveying | Werner & Pfleiderer | 135/67.5 |
| Kneading Block | Werner & Pfleiderer | KB45/5/90 |
| Kneading Block | Werner & Pfleiderer | KB45/5/60 |
| Kneading Block | Werner & Pfleiderer | KB90/5/60 |
| Kneading Block | Werner & Pfleiderer | KB45/5/30 LH |
| Turbine Mixing | Werner & Pfleiderer | TME 45/20 |
| Turbine Mixing | Werner & Pfleiderer | TME 0/20 |

Example 1

| Components | Supplier | Parts | Wt. % |
|---|---|---|---|
| PE 2075 | Rexene | 80.00 | 80.00 |
| Intersept Liquid | Intersept | 20.00 | 20.00 |

Example 2

| Components | Supplier | Parts | Wt. % |
|---|---|---|---|
| PE NA 217 | Millennium Co. | 97.00 | 97.00 |
| Intersept Liquid | Intersept | 3.00 | 3.00 |

Example 3

| Components | Supplier | Parts | Wt. % |
|---|---|---|---|
| Fortilene HG3760PP, 18MI | Solvay | 80.00 | 80.00 |
| Intersept Liquid | Intersept | 20.00 | 20.00 |

Example 4

| Components | Supplier | Parts | Wt. % |
|---|---|---|---|
| Fortilene HG3760PP, 18MI | Solvay | 20.00 | 20.00 |
| Fortilene 3907PP, 36MI | Solvay | 60.00 | 60.00 |
| Intersept Liquid | Intersept | 20.00 | 20.00 |

Example 5

| Components | Supplier | Parts | Wt. % |
|---|---|---|---|
| Crystal 207 PS, 18 MFR | Huntsman | 80.00 | 80.00 |
| Intersept Liquid | Intersept | 20.00 | 20.00 |

Example 6

| Components | Supplier | Parts | Wt. % |
|---|---|---|---|
| CTS 100 NA 1000P, SAN | Polymerland | 80.00 | 80.00 |
| Intersept Liquid | Intersept | 20.00 | 20.00 |

Example 7

| Components | Supplier | Parts | Wt. % |
|---|---|---|---|
| Tyril 100 SAN OR, CTS 100 NA 1000P* | Dow | 80.00 | 80.00 |
| Intersept Liquid | Intersept | 20.00 | 20.00 |

*From Polymerland

Example 8

| Components | Supplier | Parts | Wt. % |
|---|---|---|---|
| Fortilene HG3760PP, 18MI | Solvay | 80.00 | 80.00 |
| Intersept SF101 blend | Intersept | 20.00 | 20.00 |

Example 9

| Components | Supplier | Parts | Wt. % |
|---|---|---|---|
| PE 2075 | Rexene | 80.00 | 80.00 |
| Intersept SF101 | Intersept | 20.00 | 20.00 |

Example 10

| Components | Supplier | Parts | Wt. % |
|---|---|---|---|
| PE 2075 | Rexene | 79.93 | 79.93 |
| Intersept Liquid | Intersept | 20.00 | 20.00 |
| Smite OEM Concentrate | Medachieve Co., OH | 0.67 | 0.67 |

Example 11

| Components | Supplier | Parts | Wt. % |
|---|---|---|---|
| P5M5K-047, Random COPP, NATURAL, MFR-12 | General Polymers | 80.00 | 80.00 |
| Intersept Liquid | Intersept | 20.00 | 20.00 |

Example 12

| Components | Supplier | Parts | Wt. % |
|---|---|---|---|
| Fortilene HG 3760PP | Solvay | 96.90 | 96.90 |
| Intersept Liquid | Intersept | 3.00 | 3.00 |
| Smite OEM Concentrate | Medachieve Co., OH | 0.10 | 0.10 |

EXAMPLES 13 and 14

These examples illustrate polymer formulations for use in the formation of masterbatches where the polymer has been modified by a modifying component so as to alter the melting point or glass transition temperature of the polymer. The resulting mixture can then be used as in Examples 1–12.

Example 13

| Components | Parts | Wt.% | Supplier |
|---|---|---|---|
| Phenoxy YP50F | 70.00 | 70.00 | Tohto Kasei Co. |
| Rucoflex S-102055 | 30.00 | 30.00 | Ruco Polymer Corp. |
| Total | 100.00 | 100.00 | |

Example 14

| Components | Parts | Wt. % | Supplier |
|---|---|---|---|
| Phenoxy YP50F | 70.00 | 70.00 | Tohto Kasei Co. |
| Arylzene | 30.00 | 30.00 | Georgia Pacific |
| Total | 100.00 | 100.00 | |

EXAMPLES 15 and 16

Example 15

The following table illustrates a sample paint formulation suitable for use as an exterior white trim house paint.

| Components | Supplier | Parts | Wt. % |
|---|---|---|---|
| Water | — | 112.40 | 10.29 |
| Cellosize Hydroxyl ethyl cellulose ER-15,000 | Union Carbide | 2.00 | 0.18 |
| Ammonium Hydroxide, 28% | — | 1.90 | 0.17 |
| "Troy" 586 Biocide (for in can stability) | TroyCo. | 2.10 | 0.19 |
| "Tamol" 1124 | Tamol | 7.70 | 0.70 |
| "Colloid" 640 | Rhone-Poulenc | 2.00 | 0.18 |
| Triton Nonionic Surfactant N-57 | Union Carbide Corp. | 2.20 | 0.20 |
| Propylene glycol | — | 62.90 | 5.76 |
| "Ti-Pure" R-902 | DuPont | 247.00 | 22.60 |
| "Polygloss" 90 | J. M. Huber | 52.00 | 4.76 |
| LETDOWN | | | |
| UCAR Latex 625, acrylic emulsion. (pH = 8.5) | UCAR Emulsion Systems | 477.5 | 43.70 |
| UCAR Filmer IBT (Solvent) | UCAR Emulsion Systems | 12.00 | 1.10 |
| "Colloid" 640 | Rhone-Poulenc | 2.90 | 0.27 |
| "Troysan" Polyphase P-20T | Troy | 15.20 | 1.39 |
| "BYK" 346 | Byk | 1.10 | 0.10 |
| Water | | 80.80 | 7.39 |

Example 16

In this example according to the invention, the biocide "Troysan" Polyphase P-20T was replaced with an equal amount of biocide into forming the masterbatch of Example 5. This formulation is also useable as an exterior white trim house paint.

While the invention has been described in terms of various embodiments thereof, the invention should not be limited to such embodiments. Any differences in scope between the disclosed embodiments should in no way be interpreted to limit the invention. Moreover, various modifications, substitutions, omissions, expansions and other changes may be made in the invention without departing from the spirit of the invention. The scope of the invention should be only limited by the scope of the following claims including equivalents thereof.

That which is claimed:

1. A masterbatch composition consisting essentially of:
   (a) at least one polymer selected from polyolefins, polystyrenes, polyesters, or mixtures thereof, and
   (b) not less than 20% by weight of the composition of a liquid antimicrobial agent, wherein the masterbatch composition is at least substantially devoid of any carrier component for the antimicrobial agent.

2. The masterbatch composition according to claim 1 wherein the polymer is a polyolefin.

3. The masterbatch composition according to claim 1 wherein the polymer is polyethylene, polypropylene, or copolymers thereof.

4. The masterbatch composition according to claim 1 wherein the antimicrobial agent is at least substantially free of heavy metals.

5. The masterbatch composition according to claim 1 wherein the antimicrobial agent comprises a mixture of alkylated phosphoric acids and ammonium salts of alkylated phosphoric acids.

6. The masterbatch composition according to claim 5 wherein the active agent is present in amount not greater than 50% by weight.

7. A masterbatch polymer composition consisting essentially of polyethylene and greater than 10% by weight of a liquid antimicrobial agent comprising substituted ammonium salts of alkylated phosphoric acids and free alkylated phosphoric acid.

8. The masterbatch polymer composition according to claim 7 wherein the antimicrobial agent is present in amount of between 20 and 50% by weight of the composition.

9. A masterbatch polymer composition consisting essentially of polypropylene and greater than 10% by weight of a liquid antimicrobial agent comprising substituted ammonium salts of alkylated phosphoric acids and free alkylated phosphoric acid.

10. The masterbatch polymer composition according to claim 9 wherein the antimicrobial agent is present in amount of between 20 and 50% by weight of the composition.

11. The masterbatch polymer composition according to claim 1 wherein the composition is in the form of pellets.

12. The masterbatch polymer composition according to claim 11 wherein the pellets have a size of about 0.01"× 0.01" to 0.15"×0.15".

13. The masterbatch polymer composition according to claim 1 wherein the composition is in the form of a powder.

14. The masterbatch polymer composition according to claim 13 wherein the particles have a size of about 15 to 200 $\mu$.

* * * * *